United States Patent [19]
Amemiya

[11] Patent Number: 5,042,491
[45] Date of Patent: Aug. 27, 1991

[54] ULTRASONIC DIAGNOSTIC APPARATUS
[75] Inventor: Shinichi Amemiya, Yokohama, Japan
[73] Assignee: Fujitsu Limited, Kawasaki, Japan
[21] Appl. No.: 466,662
[22] Filed: Jan. 17, 1990
[30] Foreign Application Priority Data
  Jan. 17, 1989 [JP] Japan .................................. 1-8065
[51] Int. Cl.⁵ .............................................. A61B 8/06
[52] U.S. Cl. ............................ 128/661.09; 73/861.25; 358/81
[58] Field of Search ................ 128/661.09; 73/861.25; 358/81

[56] References Cited
U.S. PATENT DOCUMENTS

| | | | |
|---|---|---|---|
| 4,641,668 | 2/1987 | Namekawa ..................... | 128/661.09 |
| 4,850,364 | 7/1989 | Leavitt ........................... | 128/661.09 |
| 4,911,171 | 3/1990 | Uchibori ......................... | 128/661.09 |
| 4,932,415 | 6/1990 | Angelsen et al. ............... | 128/661.09 |

Primary Examiner—Francis Jaworski
Attorney, Agent, or Firm—Staas & Halsey

[57] ABSTRACT

An ultrasonic diagnostic apparatus displays a moving body in colors. Particularly to ultrasonic analysis equipment that provides frequency and sign outputs corresponding to blood flow speed and direction by means of a color flow mapping analyzer. The average of signs analyzed by a color flow mapping analyzer is calculated to select the average sign or the sign as the result of analysis. The selection conditions are that the frequency analyzed by the color flow mapping analyzer is below is a given value and the strength analyzed thereby is below a given value. If both or any of the two conditions are met, the average sign is selected. Otherwise, the sign itself is selected. The speed distribution of a moving body is displayed on the basis of the average of selected signs and the frequency analyzed by the color flow mapping analyzer, whereby effects of noises contained in analyzed signs can be eliminated considerably.

31 Claims, 8 Drawing Sheets

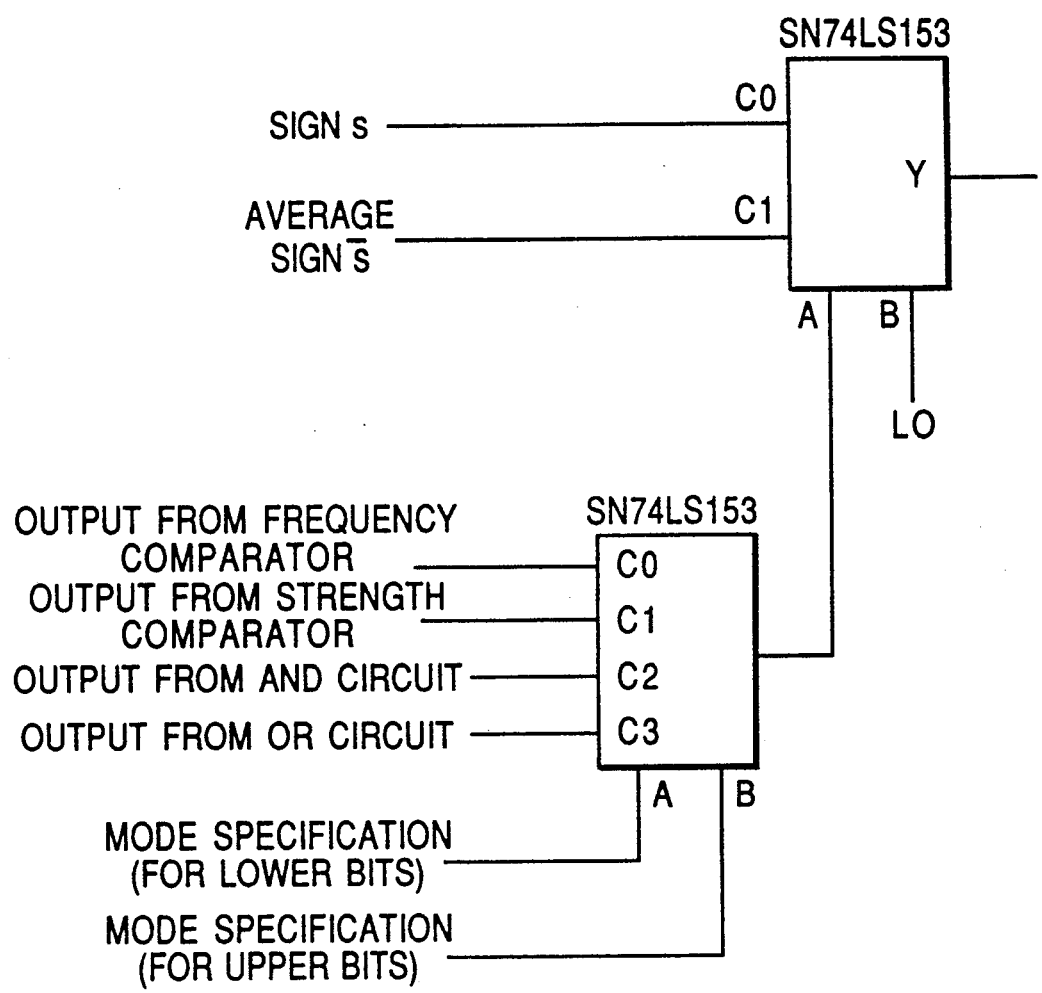

ULTRASONIC DIAGNOSTIC APPARATUS

BACKGROUND OF THE INVENTION

1. Field of the Invention

The present invention relates to ultrasonic diagnostic apparatus for displaying a moving body in color and more, particularly relates to ultrasonic analysis equipment that provides a frequency and a sign output corresponding to blood flow speed and direction by means of a color flow mapping analyzer.

2. Description of the Prior Art

Ultrasonic diagnostic apparatus utilizing a color flow mapping analyzer applies ultrasonic waves onto a human body and measures the frequency difference between the applied and reflected waves to determine the speed of blood flow. Thus, the ultrasonic diagnostic apparatus permits the easy measurement of cardiac blood flow.

A color flow mapping analyzer incorporated in the ultrasonic diagnostic apparatus orthogonally detects a received signal determined from a reflected wave by the sent signal corresponding to an applied wave and the signal whose phase is offset from the sent signal by 90 degrees to get two output signals whose phases are offset by 90 degrees from each other. After the removal of the unnecessary signals such as those from the heart wall, an auto-correlation coefficient is determined from the two output signals, X and Y. The absolute frequency value from the determined auto-correlation coefficient is output, with f, s and p denoting frequency, the positive or negative sign of the frequency from the auto-correlation coefficient, and the strength of the two output signals, X and Y, respectively. Thus, frequency f output from the color flow mapping analyzer reflects the speed of blood flow, sign s indicates its direction and strength p represents the strength of the reflected wave.

In the ultrasonic diagnostic apparatus utilizing the color flow mapping analyzer, a positive sign s output therefrom indicates the shade corresponding to frequency f, e.g., blue, and a negative sign s indicates the shade corresponding to frequency f, e.g., red to provide images covering the distribution of blood flow. If the strength p output from the color flow mapping analyzer is below a given threshold, the value of the frequency f is replaced by 0, since the SN ratio of the reflected wave is degraded. Thus, the effects of noises can be eliminated.

As a prior art of the ultrasonic diagnostic apparatus, the Japanese Patent Application, No. 48233-1987 (the Japanese Patent Publication Open to Public Inspection, No. 270139-1987) is known.

The prior art is such that, if strength p output from the color flow mapping analyzer is below a given threshold, frequency f is replaced by 0; since a too high threshold set results in degraded image quality (black-holes appear in the image), however, a threshold is set within allowable measuring accuracy. Thus, frequency f output from the color flow mapping analyzer corresponding to strength near a threshold contains slight noises, making it impossible to completely eliminate its effects.

Contained noises lead to random values of frequency f and sign s, causing the partial inversion of values of sign s. A result is the occurrence of the problem that the blue color indicating that blood flows in a certain direction is mixed with red colors and images are disordered. Such disorder may result in improper diagnosis in hospitals which use the ultrasonic diagnostic apparatus of the prior art.

A possible method to solve the disorder of images caused by the inversion of sign s by noises is such that signs s in a given area are averaged to compensate for local variations in sign s. Although, in general, low-speed blood flow encounters no reverse flow, however, the fact is observed that high-speed blood flow classified into turbulent flow involves local reverse flow. Thus, the compensation for image quality by averaging signs s also makes uniform local reverse flow caused by turbulent flow. Hence, such compensation cannot be applied actually.

SUMMARY OF THE INVENTION

An object of the present invention is to prevent images from being disordered by noises.

Another object of the present invention is to prevent false diagnosis originating in images.

The present invention is characterized by the introduction of at least one of frequency and strength comparators and the control of selection by a sign selection circuit according to the output of the comparators. The sign selection circuit receives the signs output from the color flow mapping analyzer and the average thereof, selecting and outputting said signs or the average. The selection conditions are that the frequency analyzed by the color flow mapping analyzer is below a certain value, that the strength analyzed by the color flow mapping analyzer is over a certain value, that both of these two conditions are met, and that at least one of the conditions is met. In each case, the average of signs is selected and, in the other cases, a sign itself as an analysis result is selected.

BRIEF DESCRIPTION OF THE DRAWINGS

FIG. 8 provides the configuration of a sample sign selection circuit and a sample selection circuit in the mode control circuit in the preferred embodiment;

DESCRIPTION OF THE PREFERRED EMBODIMENT OF THE INVENTION

Figure 1:
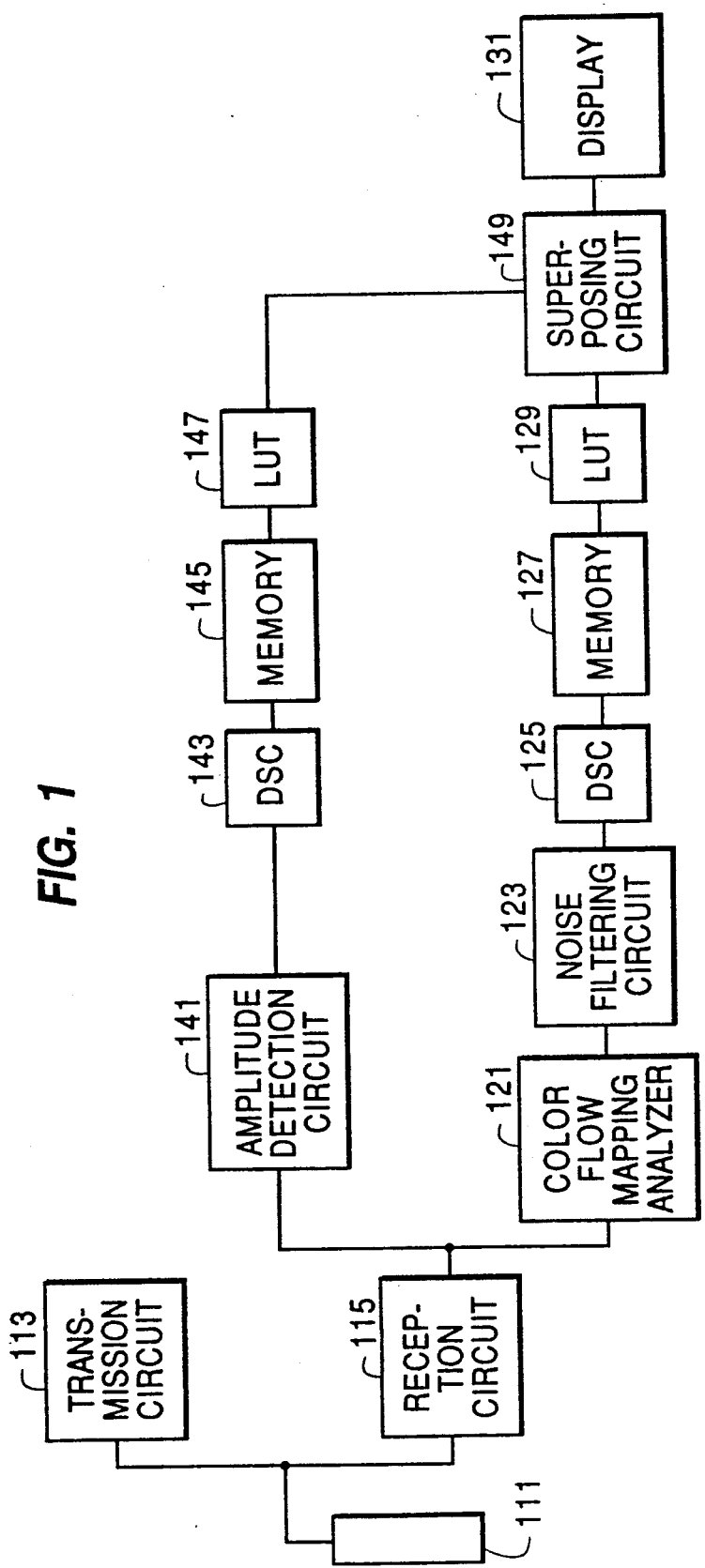
FIG. 1 illustrates the configuration of a preferred embodiment of ultrasonic diagnostic apparatus of the present invention.

In FIG. 1, 111 stands for an ultrasonic probe, 113 for a transmission circuit, 115 for a reception circuit, 121 for a color flow mapping analyzer, 123 for a noise filtering circuit, 125 and 143 for digital scanning converters, 127 and 145 for memory, 129 and 147 for look-up tables, 131 for a display, 141 for an amplitude detection circuit, and 149 for a superposing circuit.

Ultrasonic probe 111 has the configuration called e.g., a phased array, being provided with about several dozen ultrasonic elements. Ultrasonic probe 111 is connected to transmission circuit 113 and reception circuit 115.

Transmission circuit 113, which drives ultrasonic probe 111, excites the ultrasonic elements incorporated in the same to generate ultrasonic waves with a certain irradiation angle. Reception circuit 115 which is used to detect ultrasonic waves reflected by an object to be measured (moving body) when they reach ultrasonic probe 111, delays and adds the signals from ultrasonic elements in order for the detection of the reflected waves.

Color flow mapping analyzer 121 analyzes the speed of an object measured in accordance with signals received from reception circuit 115. After its analysis, color flow mapping analyzer 121 generates frequency output f corresponding to the speed of the object measured, sign s corresponding to the speed direction, and strength p corresponding to the strength of reflected waves. Output from the color flow mapping analyzer is entered into noise filtering circuit 123.

Noise filtering circuit 123 corrects sign s output from color flow mapping analyzer 121 in accordance with a certain preset mode. This correction is against the inversion of a sign by noises. When a state where the sign may be inverted by noises is detected, mean value $\bar{s}$ of a required period is output in place of sign s. In that case, the signs of e.g. 15 successive pixels before and after a pixel displayed are averaged to determine the sign of one pixel contained in the 15 pixels. Sign s output from noise filtering circuit 123, or its average value $\bar{s}$ and frequency f are entered into digital scanning converter 125.

Digital scanning converter 125 is for sequentially scanning and fetching output from noise filtering circuit 123. The fetched data is entered into memory 127. The scanning by digital scanning converter 125 is sync with scanning which fetches reflected waves from ultrasonic probe 111. Memory 127 sequentially stores data output from digital scanning converter 125 into the addresses corresponding to the positions of the object measured. The data stored in memory 127 is sequentially read and entered into look-up table 129.

Look-up table 129 creates color data (e.g., RGB data) on the basis of data read from memory 127. Memory 127 stores frequencies f and signs s or its average value $\bar{s}$ output from noise filtering circuit 123. The stored data is converted into color data on the speed of the object measured. E.g., positive sign s or average value $\bar{s}$ corresponds to red, and color data is obtained by making the blade of the red correspond to frequency f. On the contrary, negative sign s or average value $\bar{s}$ corresponds to blue, and color data is obtained by making the blade of the blue correspond to frequency f. The obtained color data is entered into display 131.

Display 131 displays the speed of the object measured in color on the basis of color data output from look-up table 129. E.g., assuming that the object measured is blood, blood flow in a certain direction is displayed in red or blue. High-speed flow called turbulent flow sometimes inverts its flow direction, being displayed by a mixture of blue and red.

Display 131 is applicable to the indication of blood flow. The shape of an object can be measured using reflected ultrasonic waves. The following description covers shape measurement.

Amplitude detection circuit 141 detects the amplitude of a signal received from reception circuit 115. Amplitude detection circuit 141 provides the output corresponding to the amplitude of a received signal, i.e., the detected output corresponding to the strength of a reflected wave reaching ultrasonic wave probe 111. The detected output is scanned by digital scanning converter 143, stored into memory 145, and entered into look-up table 147. Look-up table 147 creates monochromatic data (with the same RGB value) using data read from memory 145. E.g., applying ultrasonic waves to the cross section of a heart results in different detected output from amplitude detection circuit 141, since the strength of reflected waves is different between the heart wall and the inner section through which blood flows. This difference is displayed on display 131 as the shape of an object measured. Superposing circuit 149 superposes output from tables 129 and 147 for supply to display 131.

Described below is a description of the detailed configuration and operation of the above preferred embodiment on the basis of FIGS. 2 thru 10.

Figure 2:
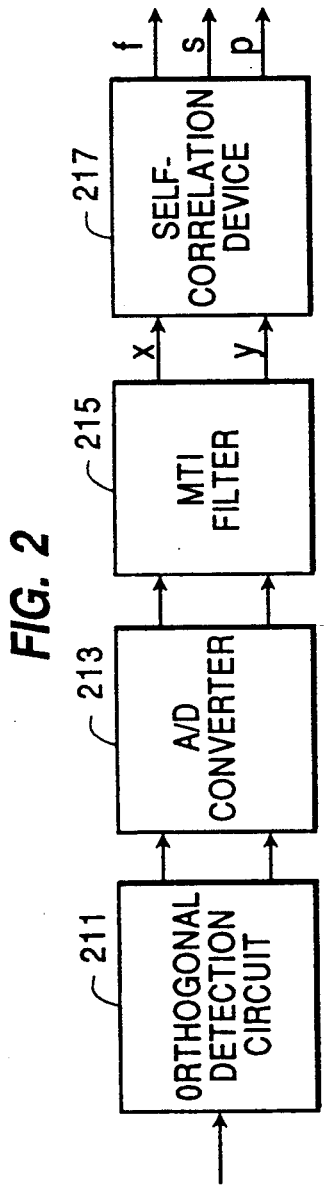
FIG. 2 illustrates the detailed configuration of the color flow mapping analyzer in the preferred embodiment.

FIG. 2 shows the detailed configuration of color flow mapping analyzer 121. 211 stands for orthogonal detection circuit, 213 for an analog/digital (A/D) converter, 215 for a motion target indicator (MTI) filter, and 217 for an auto-correlation device.

Orthogonal detection circuit 211 orthogonally detects received output from reception circuit 115 by means of a signal with the same frequency as output frequency fc of an applied wave and a signal with the frequency offset from output frequency fc by 90 degrees. This orthogonal detection provides two output signals whose phases are offset by 90 degrees from each other, which signals are entered into A/D converter 213.

A/D converter 213 converts the two entered signals into their corresponding digital data. The obtained digital data is entered into MTI filter 215.

MTI filter 215 serves as a high pass filter for two pieces of digital data entered from A/D converter 213. E.g., if ultrasonic probe 111 has repeatedly received reflected waves on the same position of an object measured and if MTI filter 215 has subtracted the two waves, MTI filter 215 serves as a one-degree high pass filter for the output data from A/D converter 213 corresponding to the above reflected waves. Thus, the movement of an object measured leads to higher output values from MTI filter 215, depending on the movement speed. Two pieces of output from MTI filter 215 are entered into auto-correlation device 217.

Auto-correlation device 217 determines a frequency from auto-correlation on the basis of two pieces of output from MTI filter 215. Assuming that the frequency determined from auto-correlation is F and two pieces of output delivered from MTI filter 215 are X(i) and Y(i) (where i refers to the number of transmissions and receptions repeated on the same position of an object measured), the frequency obtained from auto-correlation is:

$$F = \frac{1}{T} \tan^{-1}\left\{ \frac{\Sigma(X(i)Y(i-1) - Y(i)X(i-1))}{\Sigma(X(i)X(i-1) + Y(i)Y(i-1))} \right\} \quad (1)$$

where T indicates the period of repeated transmission or reception repeated on the same position of the object measured.

Auto-correlation device 217 produces absolute value |F| of the frequency determined from auto-correlation according to expression (1), as frequency F, and the sign of auto-correlation coefficient F, as s. Auto-correlation device 217 produces the total of the square sum of X(i) and Y(i), $\Sigma(X(i)^2 + Y(i)^2)$, corresponding to the same position of the object measured, as strength p, which expresses the strength of reflected waves. The output from auto-correlation device 217 is entered into noise filtering circuit 123.

Figure 3:
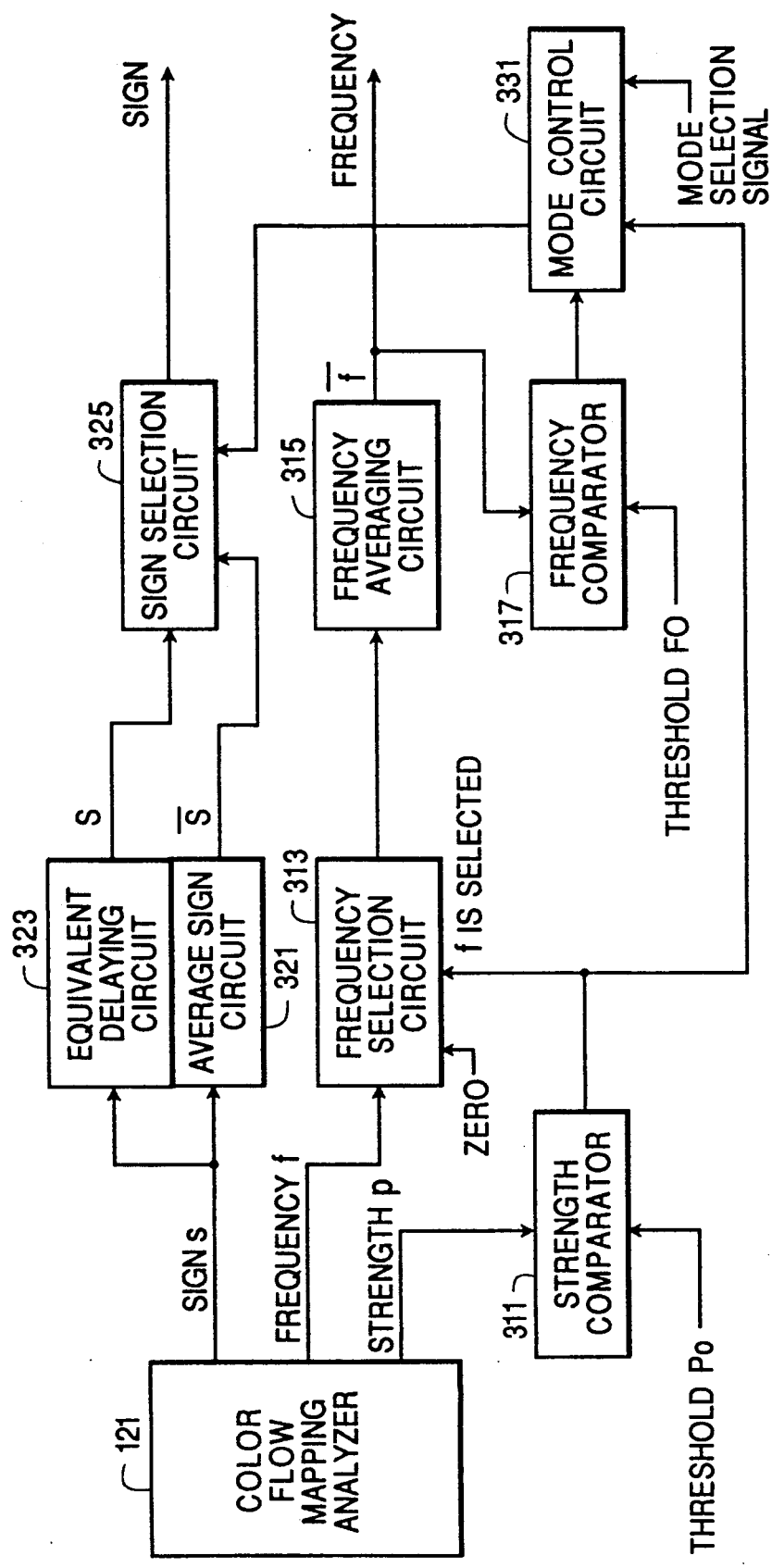
FIG. 3 illustrates the detailed configuration of a noise filtering circuit in the preferred embodiment.

FIG. 3 shows the detailed configuration of noise filtering circuit, where 311 stands for a strength comparator, 313 for a frequency selection circuit, 315 for a frequency averaging circuit, 317 for a frequency comparator, 321 for an average sign circuit, 323 for an equivalent delaying circuit, 325 for a sign selection circuit, and 331 for a mode control circuit.

Strength comparator 311 receives strength p from auto-correlation device 217 in color flow mapping analyzer 121, and compares the strength with given threshold Po on their magnitude. The result of this comparison is entered into frequency selection circuit 313 and mode control circuit 331.

Frequency selection circuit 313 receives frequency f from auto-correlation device 217 in color flow mapping analyzer 121. Frequency selection circuit 313 outputs frequency f as it is or replaces the frequency with 0, depending on the result of comparison by strength comparator 311. Concretely, if strength p entered into strength comparator 311 is below threshold Po, frequency f is affected significantly by noises and, thus, the frequency is replaced with 0 for output. In the other cases, frequency f is output, as it is. The output from frequency selection circuit 313 is entered into frequency averaging circuit 315.

Frequency averaging circuit 315 determines the average value of movement in a given period from output from frequency selection circuit 313 to output average frequency $\bar{f}$. Determining average frequency $\bar{f}$ from frequency f makes possible the correction of images by correlation, permitting easy to see indication by display 131. The output from frequency averaging circuit 315 is entered into frequency comparator 317 and submitted outside noise filtering circuit 123.

Frequency comparator 317 compares entered average frequency $\bar{f}$ with given threshold Fo for their magnitude. The result of this comparison is entered into mode control circuit 331.

Mode control circuit 331 controls selection by sign selection circuit 325 in accordance with output from strength comparator 311 and/or output from frequency comparator 317.

Depending on the mode selection signal entered into mode control circuit 331, the control mode is selected and the control signal conforming to the set control mode is entered into sign selection circuit 325.

Average sign circuit 321 and equivalent delaying circuit 323 receive sign s output from auto-correlation device 217 in color flow mapping analyzer 121. Average sign circuit 321 calculates and outputs average sign s during a certain period. The average sign covers the pixels displayed; e.g., the signs of 7 successive pixels are averaged for output as average sign $\bar{s}$. Average sign $\bar{s}$ output from average sign circuit 321 is entered into sign selection circuit 325. Equivalent delaying circuit 323 is for synchronization with the period taken by average sign circuit 321 to calculate the average sign. Entered sign s is delayed over a certain period for output. Sign s delayed by equivalent delaying circuit is entered into sign selection circuit 325.

Sign selection circuit selects and outputs one of average sign $\bar{s}$ received from sign circuit 321 and sign s received from equivalent delaying circuit 323. This selection is controlled by a control signal entered from mode control circuit 331. Sign s or average sign $\bar{s}$ output from sign selection circuit is delivered outside noise filtering circuit 123.

Table 1 shows details of the control modes dealt with in mode control circuit 331. Given below is a description of the control modes.

TABLE 1

|  | Input signal | Selection |
|---|---|---|
| Mode 1 | $\bar{f} >$ Fo | s |
|  | $\bar{f} \leq$ Fo | $\bar{s}$ |
| Mode 2 | p > Po | s |
|  | p ≤ Po | $\bar{s}$ |
| Mode 3 | Modes 1 and 2 |  |
|  | ($\bar{f} >$ Fo) ∩ (p > Po) | s |
|  | Other cases | $\bar{s}$ |
| Mode 4 | Mode 1 or 2 |  |
|  | ($\bar{f} >$ Fo) ∪ (p > Po) | s |
|  | Other cases | $\bar{s}$ |

As well known, little reverse flow exists with blood flowing at low speed. Control mode 1 takes advantage of this nature.

Mode control circuit 331 that has received the mode selection signal corresponding to mode 1 selects average sign $\bar{s}$, when average frequency $\bar{f}$ is below given threshold Fo, and selects sign s in the other cases. Since frequency comparator 317 compares average frequency $\bar{f}$ with given threshold Fo, mode control circuit 331 controls selection in sign selection circuit 325 on the basis of the result of this comparison.

Thus, in mode 1, noise filtering circuit 123 outputs average sign $\bar{s}$ in place of sign s, if an object measured is moving at low speed, and outputs sign s in the other cases. Little reverse flow exists at low speed. This allows replacement by average sign $\bar{f}$ without any substantial trouble.

Mode control circuit 331 that has received the mode selection signal corresponding to mode 2 selects average sign $\bar{s}$, when strength p is below given threshold Po, and selects sign s in the other cases. Since strength comparator 311 compares strength p with given threshold Po, mode control circuit 331 controls selection by sign selection circuit 325 on the basis of the result of this comparison.

Thus, in mode 2, noise filtering circuit 123 outputs average sign $\bar{s}$, when few waves are reflected by an object measured and strength p is low, and outputs sign s in the other cases. Low strength p indicates that no significant waves are reflected. This allows replacement by average sign $\bar{s}$ without any substantial trouble.

Mode control circuit 331 that has received the mode selection signal corresponding to mode 3 selects average sign $\bar{s}$, when average frequency $\bar{f}$ is below given threshold Fo and strength p is below given threshold Po, and selects sign s in the other cases. Mode control circuit 331 controls selection by sign selection circuit 325 on the basis of the results of comparison in both of frequency comparator 317 and strength comparator 325.

Mode control circuit 331 that has received the mode selection signal corresponding to mode 4 selects average sign s̄, when any of the conditions that average frequency f̄ is below given threshold Fo and strength p is below given threshold Po is met, and selects sign s in the other cases (average frequency f̄ is over given threshold Fo and strength p is over given threshold Po). Mode control circuit 331 controls selection by sign selection circuit 325 on the basis of the results of comparison by both of frequency comparator 317 and strength comparator 311.

Thus, average sign s̄ is selected instead of sign s in mode 1 when an object measured is moving at low speed, in mode 2 when low amplitude waves are reflected, in mode 3 when both of these conditions are met, and in mode 4 when any of them is met. Noise filtering circuit 123 outputs selected sign (s or s̄) and average frequency f̄, and display 131 placed in the subsequent stage uses each piece of this output for indication. Based on selected sign (s or s̄), indication by display 131 is clean, with noise effects removed.

The removal of noises in indication by display 131 presents hospital staff from being worried by noises and thus from false diagnosis.

Figure 4:
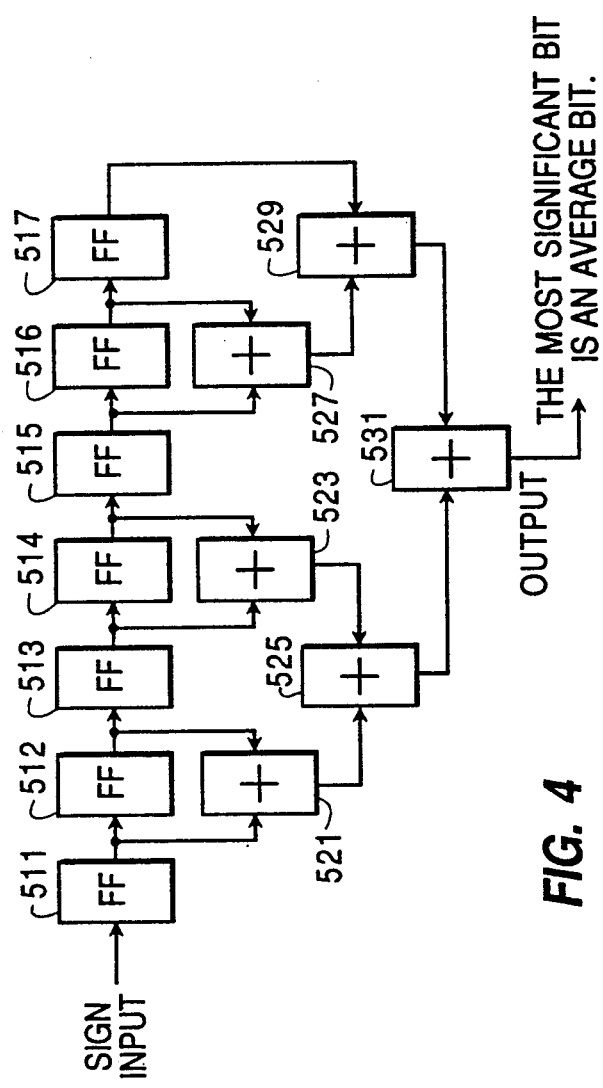
FIG. 4 illustrates the detailed configuration of a sign averaging circuit in the preferred embodiment.

FIG. 4 shows the detailed configuration of average sign circuit 321. Here, 511, 512, 513, 514, 515, 516 and 517 stand for flip-flops (FFs), and 521, 523, 525, 527, 529 and 531 for adders.

E.g., sign s consists of 1 bit of data, with "1" and "0" corresponding to positive and negative signs, respectively. Average sign circuit 321 averages 7 cycles of signs s. Seven flip-flops 511 thru 517 are connected in series.

The output terminals of flip-flops 511 and 512 are connected to the two input terminals of adder 521. The output terminals of flip-flops 513 and 514 are connected to the two input terminals of adder 523. The output terminals of flip-flops 515 and 516 are the two input terminals of adder 527. The output terminal of flip-flop 517 and that of adder 527 are connected to the two input terminals of adder 529. The output terminals of address 521 and 523 are connected to the two input terminals of adder 525. The output terminals of adders 525 and 529 are connected to the two input terminals of adder 531.

Thus, the sequential entry of signs s into flip-flop 511 leads to the addition by adder 531 of each piece of the output of the seven serially connected flip-flops, with the most significant bit of the result (consisting of 3 bits) generated as average sign s̄. Actually, if the result of the addition is not less than "100" (4 in decimal number), "1" is output and, if the result is less than "100", "0" is output as average sign s̄.

Figure 5:
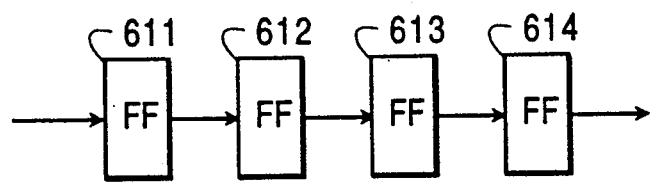
FIG. 5 illustrates the detailed configuration of an equivalent delaying circuit in the preferred embodiment.

FIG. 5 shows the detailed configuration of equivalent delaying circuit 323. Here, 611, 612, 613, and 614 stand for flip-flops (FFs). Four flip-flops 611 thru 614 are connected in series, with sign s entered into flip-flop 611 output from flip-flop 614 4 cycle alter.

Figure 6:
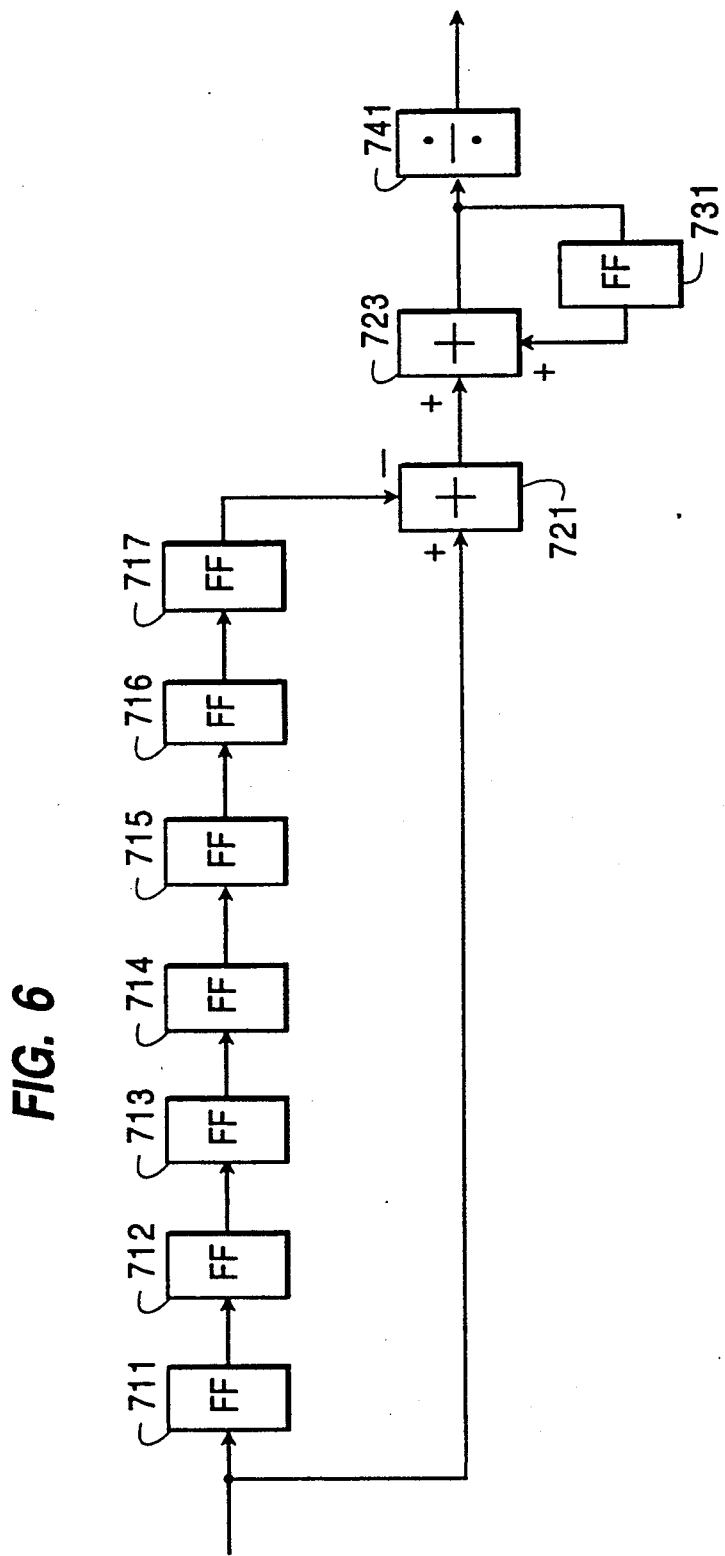
FIG. 6 illustrates the detailed configuration of a frequency averaging circuit in the preferred embodiment.

FIG. 6 shows the detailed configuration of frequency averaging circuit 315. Here, 711, 712, 713, 714, 715, 716, 717 and 731 stand for flip-flops (FFs), 721 and 723 for adders, and 741 for a divider.

Frequency f received by frequency averaging circuit 315 is entered into input terminals of flip-flop 711 and adder 721. Flip-flops 711 thru 717 are connected in series, with the output of flip-flop 717 entered into the other input terminal of adder 721, which is an inverting one. Adder 721 subtracts the output of flip-flop 717 entered into the other input terminal from frequency f entered into the one input terminal.

The output terminal of adder 721 is connected to one input terminal of adder 723, and the output terminal of adder 723 is connected to the input terminal of divider 741 and to the other input terminal of adder 723 via flip-flop 731. The output of adder 723, after it has been stored in flip-flop 731, is entered again into adder 723 itself, resulting in the accumulation of the output of adder 721. Such configuration always permits the determination of the value of accumulating frequencies f over cycles corresponding to the number of flip-flops 711 thru 717.

Divider 741 divides the output of adder 723 by the number of flip-flops 711 thru 717 (7), providing average frequency f̄ as the result of this division.

The result of adding each piece of output from flip-flops 711 thru 717 can be divided by a given value to determine average frequency f̄. But the configuration shown in FIG. 6 permits the number of adders used to be reduced. Setting the number of flip-flops to be connected in series at a multiple of 2 permits the performance of division by divider 741 as bit operation, making it possible to further simplify the configuration.

Figure 7:
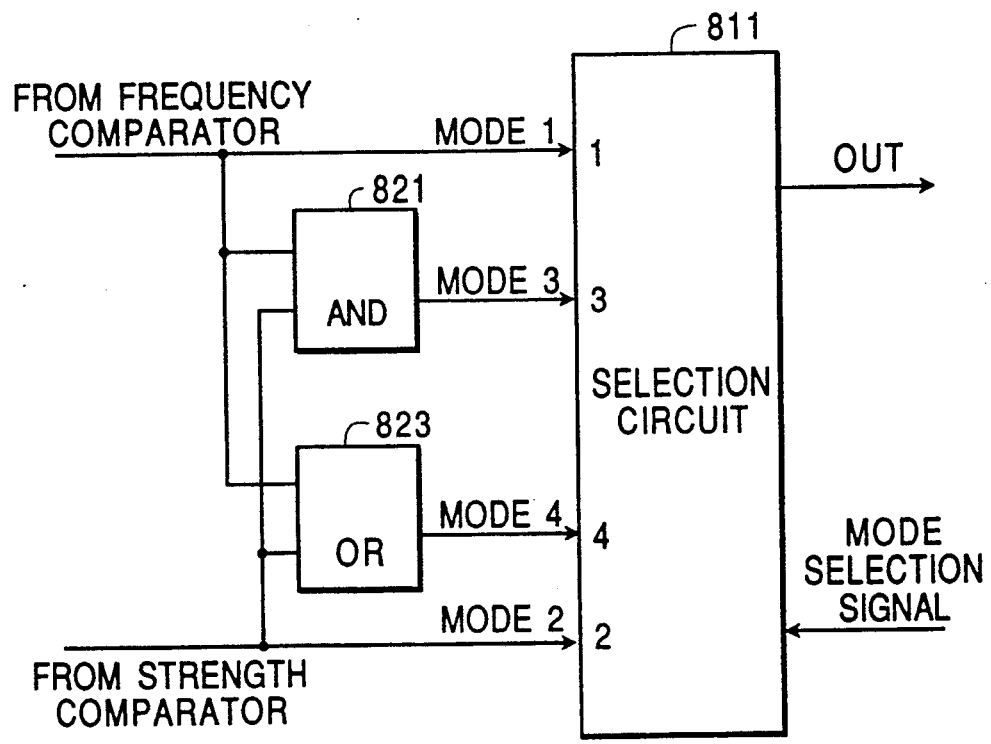
FIG. 7 illustrates the detailed configuration of a mode control circuit in the preferred embodiment.

FIG. 7 shows the detailed configuration of mode control circuit 331, where 811 stands for a selection circuit, 821 for an AND circuit, and 823 for an OR circuit.

Frequency comparator 317 is designed to output "1", if frequency f is below given threshold Fo, and "0" in the other cases. Also, strength comparator 311 is designed to output "1", if strength p is below given threshold Po, and "0" in the other cases.

The output of frequency comparator 317 is entered into the first input terminal of selection circuit 811, one input terminal of AND circuit 821, and one input terminal of OR circuit 823. The output of strength comparator 311 is entered into the second input terminal of selection circuit 811, the other input terminal of AND circuit 821, and the other input terminal of OR circuit 823. The output of AND circuit 821 is entered into the third input terminal of selection circuit 811 and that of OR circuit 823 into the fourth input terminal of selection circuit 811.

Selection circuit 811 is provided with a control terminal for receiving mode selection signals in addition to the above four input terminals. Selection circuit 811 selects the signal entered into the first input terminal, when the mode selection signal indicating mode 1 is entered into the control terminal. It selects the signal entered into the second input terminal, when the mode selection signal indicating mode 2 is entered into the control terminal. It select the signal entered into the third input terminal, when the mode selection signal indicating mode 3 is entered into the control terminal. It selects the signal entered into the fourth input terminal, when the mode selection signal indicating mode 4 is entered into the control terminal.

Sign selection circuit 325 provides selection based on output from said selection circuit 811. It selects average sign s̄ output from average sign circuit 321, when selection circuit 811 outputs "1", and sign s output from equivalent delaying circuit 323 in the other cases.

FIG. 8 shows the configuration of sign selection circuit 325 and selection circuit 811 in mode control circuit 331 implemented using standard logic SN74LS153 (data selector) manufactured by Texas Instruments (TI) Inc. The standard logic can select one of four input terminals C0 thru C3 in accordance with the input logic of input terminals A and B. Four bits "00" thru "11" corresponding to modes 1 thru 4 are entered into input terminals A and B. Sign selection circuit 325, which covers the above two pieces of input, uses C0 and C1 of the four input terminals to provide selection in accordance with the input logic of input terminal A (Input terminal B continues to receive a fixed low level signal.).

Strength comparator 311 and frequency comparator 317 can be implemented using standard logics, SN74LS682 thru 685 (magnitude comparators), manufactured by Texas Instruments (TI) Inc. In that case, P is an input value of frequency or strength and Q is a set value for comparison (threshold Po or Fo, with P>Q (pin 1) obtained as the output.

Figure 9:
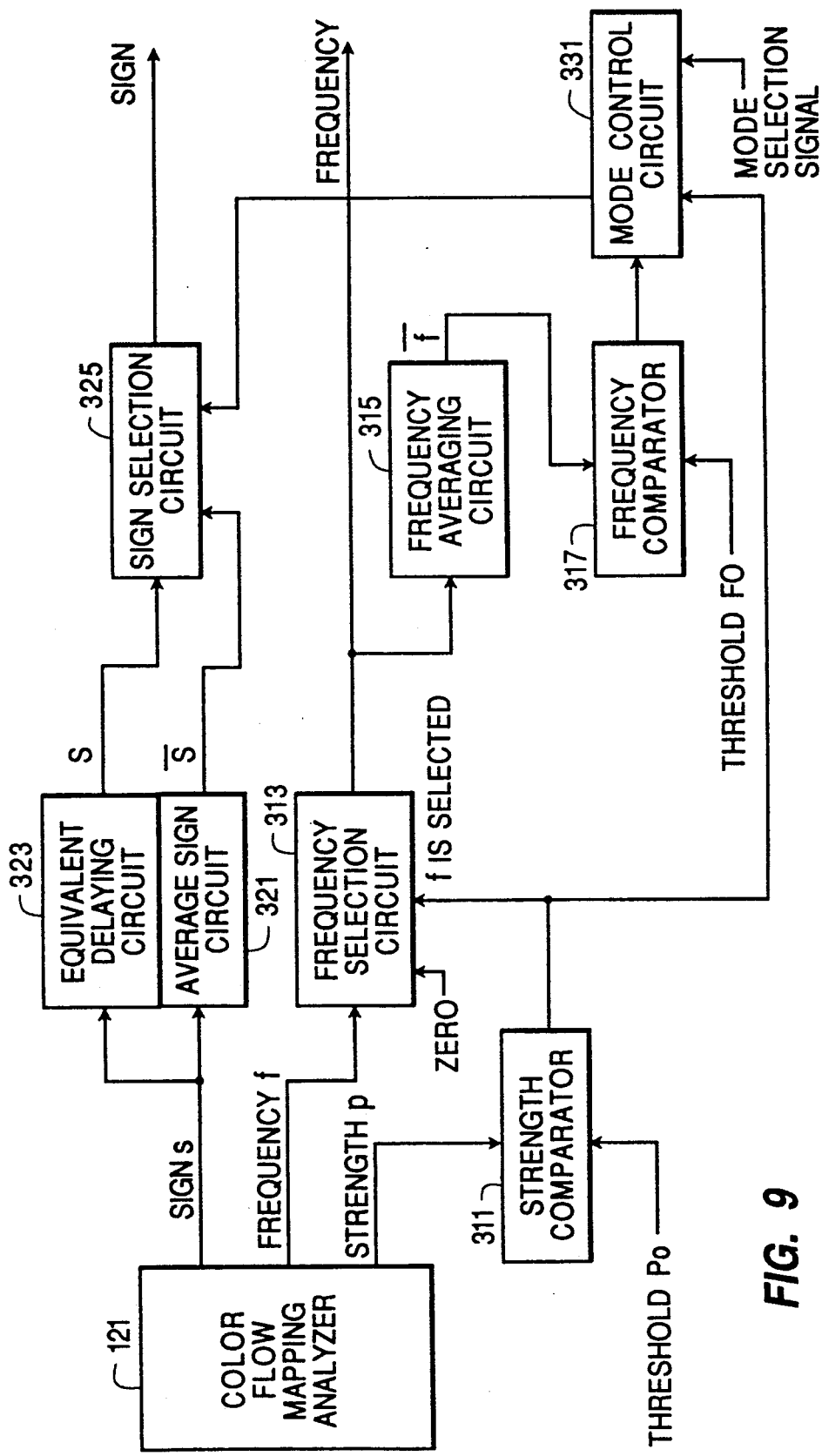
FIG. 9 illustrates the configuration of another preferred embodiment of the ultrasonic diagnostic apparatus of the present invention.

FIG. 9 shows another sample configuration of noise filtering circuit 123. While the configuration shown in FIG. 3 uses the output of frequency averaging circuit 315 and sign selection circuit 325 as the output of noise filtering circuit 123, the configuration shown in FIG. 9 uses the output of frequency selection circuit 313 and sign selection circuit 325 as the output of noise filtering circuit 123.

In the configuration shown in FIG. 9 where direct output is obtained from frequency selection circuit 313, output frequency f may contain noise elements. However, strength p corresponds to a threshold greater than given Po, causing no substantial trouble. Thus, in each of modes 1 thru 4, color indications can be obtained on the basis of selected average sign $\bar{s}$ and frequency f without any effect of noises, providing clean images. Hence, false diagnosis in hospitals can be prevented.

Figure 10:
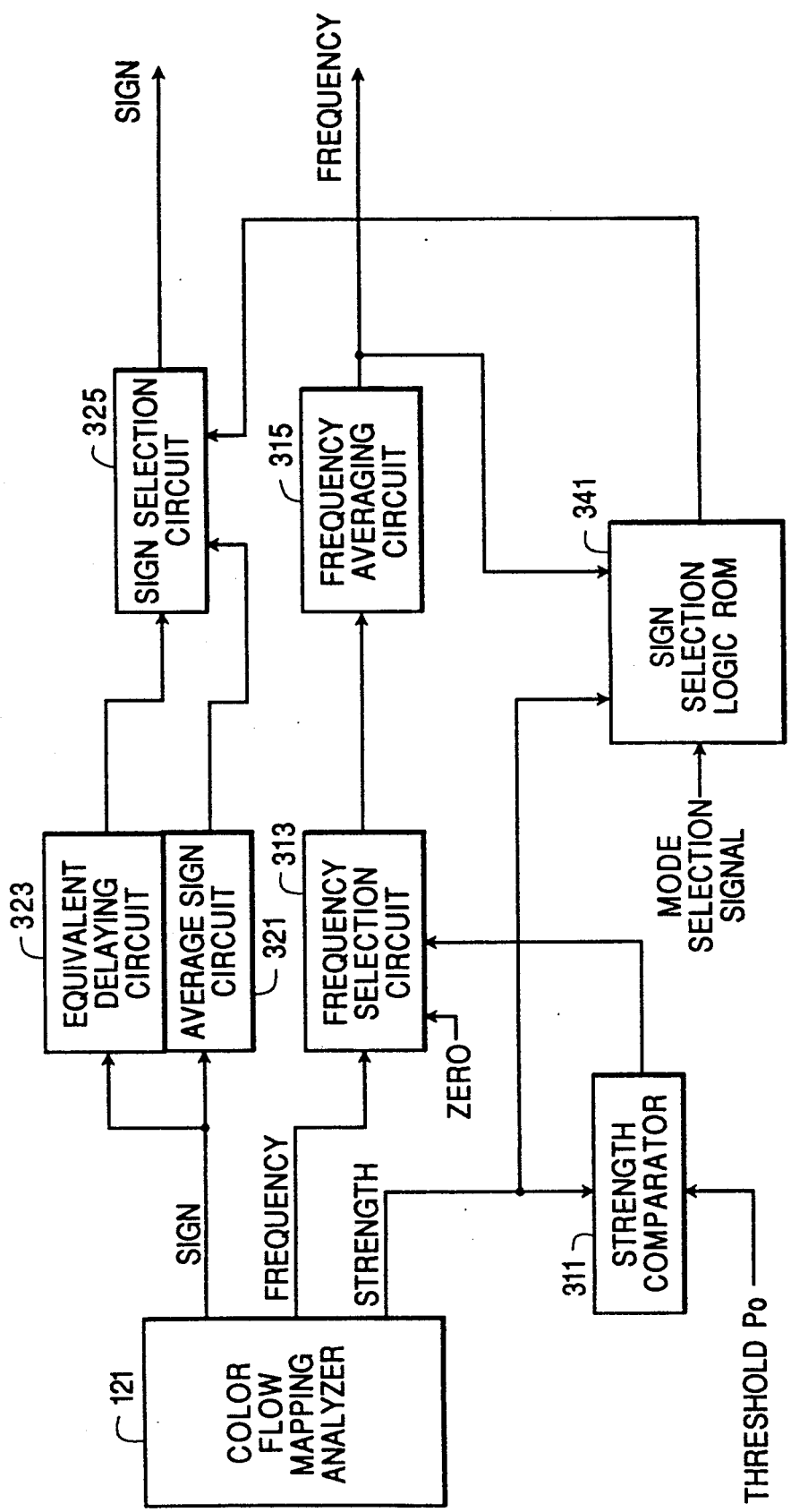
FIG. 10 illustrates the configuration of another preferred embodiment of the ultrasonic diagnostic apparatus of the present invention.

FIG. 10 shows another configuration of noise filtering circuit 123. In the configuration shown in FIG. 10, frequency comparator 317 and mode control circuit 331 in FIG. 3 are replaced by sign selection logic ROM 341. With selection information in Table 1 stored in sign selection logic ROM 341, various pieces of data needed to specify the modes and select a sign are entered as addresses to have the corresponding selection signals output. E.g., assuming that average frequency $\bar{f}$ generated by frequency averaging circuit 315 consists of 3 bits of data, the 3 bits of data, 1 bit of data corresponding to the result of comparison by strength comparator 311, and 2 bits of data specifying mode selection (total of 6 bits of data) are entered into sign selection logic ROM 341 as addresses to have 1 bit of data specifying average sign $\bar{s}$ or sign s output. Above sign selection logic ROM 341 may be replaced by other semiconductor memory such as a RAM. In the above configuration, one of modes 1 thru 4 is selected by mode control circuit 331 or sign selection logic 341 to cover all the modes. When only one mode is selected fixedly, mode control circuit 331 or sign selection logic ROM 341 may be omitted. In that case, the fixed control of mode 1 is accomplished e.g. by entering the output of frequency comparator 317 directly into sign selection circuit 325. The fixed control of mode 2 is accomplished by entering the output of strength comparator 311 directly into sign selection circuit 325. The fixed control of mode 3 is accomplished by entering the result of logically ANDing the output of strength comparator 311 and that of frequency comparator 317 into sign selection circuit 325. The fixed control of mode 4 is accomplished by entering the result of logically ORing the output of strength comparator 311 and that of frequency comparator 317 into sign selection circuit 325.

In the configuration shown in FIG. 10, noise filtering circuit 123 delivers average frequency $\bar{f}$ output from frequency averaging circuit 315 to the outside. As shown in FIG. 9, however, frequency f as the output of frequency selection circuit 313 may also be delivered to the outside.

What is claimed is:

1. An ultrasonic diagnostic apparatus for analyzing a moving body, comprising:

a color flow mapping analyzer for outputting a sign signal corresponding to a direction of movement of the moving body and a frequency signal corresponding to a speed of the moving body on the basis of received ultrasonic signals reflected from the moving body;

an average sign circuit connected to said color flow mapping analyzer for calculating over a given period of time an average of the sign signal output from said color flow mapping analyzer;

a frequency averaging circuit connected to said color flow mapping analyzer for calculating over a given period of time an average of the frequency signal output from said color flow mapping analyzer;

a frequency comparator connected to said frequency averaging circuit for comparing magnitudes of the average of the frequency signal calculated by said frequency averaging circuit with a given frequency threshold; and a sign selection circuit, connected to said color flow mapping analyzer, said average sign circuit and said frequency comparator, for outputting the sign signal output from said color flow mapping analyzer if the average frequency calculated by said frequency averaging circuit is higher than said given threshold, and outputting the average of the sign signal calculated by said average sign circuit if the average of the frequency signal calculated by said frequency averaging circuit is lower than the given frequency threshold; and a display connected to said frequency averaging circuit and said sign selection circuit for displaying a speed distribution of the moving body in dependence upon an output selected by said sign selection circuit and the average of the frequency signal calculated by said frequency averaging circuit.

2. An ultrasonic diagnostic apparatus for analyzing a moving body, comprising:

a color flow mapping analyzer for outputting a sign signal corresponding to a direction of movement of the moving body and a frequency signal corresponding to a speed of the moving body on the basis of received ultrasonic signals reflected from the moving body;

an average sign circuit connected to said color flow mapping analyzer for calculating over a given period of time an average of the sign signal output from said color flow mapping analyzer;

a frequency averaging circuit connected to said color flow mapping analyzer for calculating over a given period of time an average of the frequency signal output from said color flow mapping analyzer;

a frequency comparator connected to said frequency averaging circuit for comparing magnitudes of the average of the frequency signal calculated by said frequency averaging circuit with a given frequency threshold; and a sign selection circuit, connected to said color flow mapping analyze, said average sign circuit and said frequency comparator, for outputting the sign signal output from said color flow mapping analyzer if the average of the frequency signal calculated by said frequency averaging circuit is higher than the given threshold, and outputting the average of the sign signal calculated by said average sign circuit if the average of the frequency signal calculated by said frequency averaging circuit is lower than the given frequency threshold; and a display connected to said frequency averaging circuit and said sign selection circuit for displaying a speed distribution of the moving body in dependence upon an output selected by said sign selection circuit and the frequency signal output from said color flow mapping analyzer.

3. An apparatus as set forth in claim 1, wherein said frequency comparator is configured of sign selection logic memory having stored therein data representing results of comparing magnitudes of average frequency signals and the given frequency threshold, said sign selection logic memory receiving as an address the average of the frequency signal calculated by said frequency averaging circuit and, based on the address, outputting data to said sign selection circuit for specifying selection conditions.

4. An apparatus as set forth in claim 3, wherein said sign selection logic memory is one of a ROM and a RAM.

5. An apparatus as set forth in claim 2, wherein said frequency comparator is configured of sign selection logic memory having stored therein data representing results of comparing magnitudes of average frequency signals and the given frequency threshold, said sign selection logic memory receiving as an address the average of the frequency signal calculated by said frequency averaging circuit and, based on the address, outputting data to said sign selection circuit for specifying selector conditions.

6. An apparatus as set forth in claim 5, wherein said sign selection logic memory is one of a ROM and a ROM.

7. An ultrasonic diagnostic apparatus for analyzing a moving body, comprising:

a color flow mapping analyzer for outputting a sign signal corresponding to a direction of movement of the moving body on the basis of received ultrasonic signals reflected by the moving body, a frequency signal corresponding to a speed of the moving body, and a strength of the received ultrasonic signals;

an average sign circuit connected to said color flow mapping analyzer for calculating over a given period of time an average of the sign signal output from said color flow mapping analyzer;

a frequency averaging circuit connected to said color flow mapping analyzer for calculating over a given period of time an average of the frequency signal output from said color flow mapping analyzer;

a strength comparator connected to said color flow mapping analyzer for comparing magnitudes of the strength signal output from said color flow mapping analyzer with a given strength threshold;

a sign selection circuit, connected to said color flow mapping analyzer, said average sign circuit and said strength comparator, for outputting the sign output from said color flow mapping analyzer if the strength signal output from said color flow mapping analyzer is higher than said given strength threshold, and outputting the average of the sign signal calculated by said average sign circuit if the strength signal output said color flow mapping analyzer is lower than the strength threshold; and a display connected to said sign selection circuit and said frequency averaging circuit for displaying a speed distribution of the moving body in dependence upon an output selected by said sign selection circuit and the average of the frequency signal calculated by said frequency averaging circuit.

8. An apparatus as set forth in claim 7, wherein said sign selection circuit selects an output based on a sign selection logic memory having stored therein data representing results of comparing magnitudes of average frequency signals and the given frequency threshold, said sign selection logic memory receiving as an address the average of the frequency signal calculated by said frequency averaging circuit and, based on the address, outputting data to said sign selection circuit for specifying selection conditions.

9. An apparatus as set forth in claim 8, wherein said sign selection logic memory is one of a ROM and a RAM.

10. An ultrasonic diagnostic apparatus for analyzing a moving body, comprising:

a color flow mapping analyzer for outputting a sign signal corresponding to a direction of movement of the moving body on the basis of received ultrasonic signals reflected from the moving body, a frequency signal corresponding to a speed of the moving body, and a strength signal of the received ultrasonic signals;

an average sign circuit connected to said color flow mapping analyzer for calculating over a given period of time an average of the sign signal output from said color flow mapping analyzer;

a strength comparator connected to said color flow mapping analyzer for comparing magnitudes of the strength signal output from said color flow mapping analyzer with a given strength threshold; and a sign selecting circuit connected to said color flow mapping analyzer, said average sign circuit and said strength comparator, for outputting the sign output from said color flow mapping analyzer if the strength signal output from said color flow mapping analyzer is higher than said given strength threshold, and outputting the average of the sign signal calculated by said average sign circuit if the strength signal output said color flow mapping analyzer is lower than the given strength threshold; and a display connected to said sign selection circuit and said color flow mapping analyzer for displaying a speed distribution of the moving body in dependence upon an output selected by said sign selection circuit and the frequency signal output from said color flow mapping analyzer.

11. An ultrasonic diagnostic apparatus for analyzing a moving body, comprising:

a color flow mapping analyzer for outputting a sign signal corresponding to a direction of movement of the moving body on the basis of received ultrasonic signals reflected from the moving body, a frequency signal corresponding to a speed of the moving body, and a strength signal of the received ultrasonic signals;

an average sign circuit connected to said color flow mapping analyzer for calculating over a given period of time an average of the sign signal output from said color flow mapping analyzer;

a frequency averaging circuit connected to said color flow mapping analyzer for calculating over a given period of time an average of the frequency signal output from said color flow mapping analyzer;

a frequency comparator connected to said frequency averaging circuit for calculating magnitudes of the average of the frequency signal calculated by said frequency averaging circuit and a frequency threshold;

a strength comparator connected to said color flow mapping analyzer for comparing magnitudes of the strength signal output from said color flow mapping analyzer with a given strength threshold;

a sign selection circuit connected to said color flow mapping analyzer, said average sign circuit, said frequency comparator and said strength comparator, for outputting the sign signal output from said color flow mapping analyzer if the average of the frequency signal calculated by said frequency averaging circuit is higher than the frequency threshold and the strength signal output from said color flow mapping analyzer is higher than the strength threshold, and otherwise outputting the average of the sign signal calculated by said average sign circuit; and a display connected to said sign selection circuit and said frequency averaging circuit for displaying a speed distribution of the moving body in dependence upon an output selected by said sign selection circuit and the average of the frequency signal calculated by said frequency averaging circuit.

12. An apparatus as set forth in claim 11, wherein said frequency comparator is configured of sign selection logic memory having stored therein data representing results of comparing magnitudes of average frequency signals and the given frequency threshold, said sign selection logic memory receiving as an address the average of the frequency signal calculated by said frequency averaging circuit and, based on the address, outputting data to said sign selection circuit for specifying selection conditions.

13. An apparatus as set forth in claim 12, wherein said sign selection logic memory is one of a ROM and a RAM.

14. An ultrasonic diagnostic apparatus for analyzing a moving body, comprising:

a color flow mapping analyzer for outputting a sign signal corresponding to a direction of movement of the moving body on the basis of received ultrasonic signals reflected from the moving body, a frequency signal corresponding to a speed of the moving body, and a strength signal of the received ultrasonic signals;

an average sign circuit connected to said color flow mapping analyzer for calculating over a given period of time an average of the sign signal output from said color flow mapping analyzer;

a frequency averaging circuit connected to said color flow mapping analyzer for calculating over a given period of time an average of the frequency output from said color flow mapping analyzer;

a frequency comparator connected to said frequency averaging circuit for comparing magnitudes of the average of the frequency signal calculated by said frequency averaging circuit and a frequency threshold;

a strength comparator connected to said color flow mapping analyzer for comparing magnitudes of the strength signal output from said color flow mapping analyzer with a given strength threshold;

a sign selection circuit, connected to said color flow mapping analyzer, said average sign circuit, said frequency comparator and said strength comparator, for outputting the sign signal output from said color flow mapping analyzer if the average of the frequency signal calculated by said frequency averaging circuit is higher than the frequency threshold and the strength signal output from said color flow mapping analyzer is higher than the strength threshold, and otherwise outputting the average of the sign signal calculated by said average sign circuit; and a display connected to said sign selection circuit and said color flow mapping analyzer for displaying a speed distribution of the moving body in dependence upon an output selected by said sign selection circuit and the frequency signal output from said color flow mapping analyzer.

15. An apparatus as set forth in claim 14, wherein said frequency comparator is configured of sign selection logic memory having stored therein data representing results of comparing magnitudes of average frequency signals and the given frequency threshold, said sign selection logic memory receiving as an address the average of the frequency signal calculated by said frequency averaging circuit and, based on the address, outputting data to said sign selection circuit for specifying selection conditions.

16. An apparatus as set forth in claim 15, wherein said sign selection logic memory is one of a ROM and a RAM.

17. An ultrasonic diagnostic apparatus for analyzing a moving body, comprising:

a color flow mapping analyzer for outputting a sign signal corresponding to a direction of movement of the moving body on the basis of received ultrasonic signals reflected from the moving body, a frequency signal corresponding to a speed of the moving body, and a strength signal of the received ultrasonic signals;

an average sign circuit connected to said color flow mapping analyzer for calculating over a given period of time an average of the sign signal output from said color flow mapping analyzer;

a frequency averaging circuit connected to said color flow mapping analyzer for calculating over a given period of time an average of the frequency signal output from said color flow mapping analyzer;

a frequency comparator connected to said frequency averaging circuit for comparing magnitudes of the average of the frequency signal calculated by said frequency averaging circuit and a frequency threshold;

a strength comparator connected to said color flow mapping analyzer for comparing the strength signal output from said color flow mapping analyzer with a strength threshold;

a sign selection circuit, connected to said frequency comparator and said strength comparator, for outputting the average of the sign signal calculated by said average sign circuit if the average of the frequency signal calculated by said frequency averaging circuit is lower than the frequency threshold and the strength signal output from said color flow mapping analyzer is lower than the strength threshold, and otherwise outputting the sign output from said color flow mapping analyzer; and a display connected to said sign selection circuit and said frequency averaging circuit for displaying a speed distribution of the moving body in dependence upon an output selected by said sign selection circuit and the average of the frequency signal calculated by said frequency averaging circuit.

18. An apparatus as set forth in claim 17, wherein said frequency comparator is configured of sign selection logic memory having stored therein data representing results of comparing magnitudes of average frequency signals and the given frequency threshold, said sign selection logic memory receiving as an address the average of the frequency signal calculated by said frequency averaging circuit and, based on the address, outputting data to said sign selection circuit for specifying selection conditions.

19. An apparatus as set forth in claim 18, wherein said sign selection logic memory is one of a ROM and a RAM.

20. An ultrasonic diagnostic apparatus for analyzing a moving body, comprising:
a color flow mapping analyzer for outputting a sign signal corresponding to a direction of movement of the moving body on the basis of received ultrasonic signals reflected from the moving body, a frequency signal corresponding to a speed of the moving body, and a strength signal of the received ultrasonic signals;
an average sign circuit connected to said color flow mapping analyzer for calculating over a given period of time an average of the sign signal output from said color flow mapping analyzer;
a frequency averaging circuit connected to said color flow mapping analyzer for calculating over a given period of time an average of the frequency signal output from said color flow mapping analyzer;
a frequency comparator connected to said frequency averaging circuit for comparing magnitudes of the average of the frequency signal calculated by said frequency averaging circuit and a frequency threshold;
a strength comparator connected to said color flow mapping analyzer for comparing magnitudes of the strength signal output from said color flow mapping analyzer with a strength threshold;
a sign selection circuit, connected to said color flow mapping analyzer, said average sign circuit, said frequency comparator and said strength comparator, for outputting the average of the sign signal calculated by said average sign circuit if the average of the frequency signal calculated by said frequency averaging circuit is lower than the frequency threshold and the strength signal output from said color flow mapping analyzer is lower than the strength threshold, and otherwise outputting the sign signal output from said color flow mapping analyzer; and
a display connected to said sign selection circuit and said frequency averaging circuit for displaying a speed distribution of the moving body in dependence upon an output selected by said sign selection circuit and the average of the frequency signal calculated by said frequency averaging circuit.

21. An apparatus as set forth in claim 20, wherein said frequency comparator is configured of sign selection logic memory having stored therein data representing results of comparing magnitudes of average frequency signals and the given frequency threshold, said sign selection logic memory receiving as an address the average of the frequency signal calculated by said frequency averaging circuit and, based on the address, outputting data to said sign selection circuit for specifying selection conditions.

22. An apparatus as set forth in claim 21, wherein said sign selection logic memory is one of a ROM and a RAM.

23. An ultrasonic diagnostic apparatus comprising:
a color flow mapping analyzer for outputting a sign signal corresponding to a direction of movement of a moving body to be diagnosed;
an average sign signal circuit connected to said color flow mapping analyzer for determining an average of the sign signal over a given period; and
a sign selection circuit connected to said color flow mapping analyzer and said average sign signal circuit to selectively output one of the sign signal from said color flow mapping analyzer and the average of the sign signal.

24. An apparatus according to claim 23, further comprising a strength comparator connected to said color flow mapping analyzer for comparing a strength signal output from said color flow mapping analyzer with a predetermined strength threshold.

25. An apparatus according to claim 24,
wherein said sign selection circuit outputs the sign signal from said color flow mapping analyzer when said strength comparator indicates the strength signal is higher than the strength threshold; and
wherein said sign signal selection circuit outputs the average of the sign signal from said average sign circuit when said strength comparator indicates the strength signal is lower than the strength threshold.

26. An apparatus according to claim 23, further comprising:
a frequency averaging circuit connected to said color flow mapping analyzer to average a frequency signal, corresponding to a speed of the moving body, from said color flow mapping analyzer over a given period and to produce an average frequency; and
a frequency comparator connected to said frequency signal averaging circuit to compare the average frequency from said frequency averaging circuit with a predetermined frequency threshold.

27. An apparatus according to claim 26,
wherein said sign selection circuit outputs the sign signal from said color flow mapping analyzer when said strength comparator indicates the strength signal is higher than the frequency threshold; and
wherein said sign selection circuit outputs the average of the sign signal from said average sign circuit when said frequency comparator indicates the average frequency is lower than the frequency threshold.

28. An apparatus according to claim 26, further comprising: a strength comparator connected to said color flow mapping analyzer for comparing a strength signal output of said color flow mapping analyzer with a predetermined strength threshold.

29. An apparatus according to claim 28, wherein said sign selection circuit outputs the sign signal from said color flow mapping analyzer based on comparison by said strength comparator and comparison by said frequency comparator.

30. An apparatus according to claim 28,
wherein said sign selection circuit outputs the sign from said color flow mapping analyzer when both said strength comparator and said frequency comparator indicate the strength signal is higher than the strength threshold and the average frequency is higher than the frequency threshold; and
wherein said selection circuit outputs the average of the sign signal from said average sign circuit when both said strength signal comparator and said frequency signal comparator indicate the strength signal is higher than the strength threshold and the average frequency is higher than the frequency threshold.

31. An apparatus according to claim 28,
wherein said sign selection circuit outputs the sign signal from said color flow mapping analyzer when said strength comparator and said frequency comparator indicate only one of the following conditions—the strength signal is higher than the strength threshold and the average frequency is higher than the frequency threshold; and
wherein said sign selection circuit outputs the average of the sign signal from said average sign circuit when said strength comparator and said frequency comparator indicate only one of the following conditions—the strength signal is lower than the strength threshold and the average frequency is lower than the frequency threshold.

* * * * *

UNITED STATES PATENT AND TRADEMARK OFFICE
CERTIFICATE OF CORRECTION

PATENT NO. : 5,042,491

DATED : August 27, 1991

INVENTOR(S) : Amemiya

It is certified that error appears in the above-identified patent and that said Letters Patent is hereby corrected as shown below:

On the Title page

Item [57] Abstract, line 2, "to" should be deleted;
                               line 3, "that" should be deleted.

Col. 2, line 55, "provides" should be --illustrates--.

Col. 12, line 25, "An apparatus" should be --An ultrasonic diagnostic apparatus--.

Col. 16, line 59, "strength" (first occurrence) should be --frequency--; "strength" (second occurrence) should be --average--;

line 60, "signal" should be --frequency--.

Signed and Sealed this

Twenty-ninth Day of December, 1992

Attest:

DOUGLAS B. COMER

Attesting Officer     Acting Commissioner of Patents and Trademarks